United States Patent
Oribe et al.

(10) Patent No.: US 6,790,208 B2
(45) Date of Patent: Sep. 14, 2004

(54) ROD GRIPPER

(75) Inventors: Kazuya Oribe, Tokyo (JP); Masato Tomita, Toyohashi (JP); Hiroshi Takamido, Nagoya (JP); Noriyuki Ina, Toyohashi (JP)

(73) Assignee: Showa Ika Kohgyo Co., Ltd., Nagoya (JP)

( * ) Notice: Subject to any disclaimer, the term of this patent is extended or adjusted under 35 U.S.C. 154(b) by 0 days.

(21) Appl. No.: 09/812,461

(22) Filed: Mar. 20, 2001

(65) Prior Publication Data

US 2001/0027318 A1 Oct. 4, 2001

(30) Foreign Application Priority Data

Mar. 28, 2000 (JP) .......................................... P2000-89784

(51) Int. Cl.$^7$ .................................................. A61F 5/04
(52) U.S. Cl. .............................. 606/53; 606/54; 606/60; 606/61; 606/99; 606/104
(58) Field of Search .............................. 606/53, 54, 60, 606/61, 99, 104

(56) References Cited

U.S. PATENT DOCUMENTS

| | | | | |
|---|---|---|---|---|
| 5,020,519 A | * | 6/1991 | Hayes et al. | 128/69 |
| 5,364,397 A | * | 11/1994 | Hayes et al. | 606/61 |
| 5,391,181 A | * | 2/1995 | Johnson et al. | 606/207 |
| 5,562,447 A | * | 10/1996 | Moy et al. | 433/150 |
| 5,709,685 A | * | 1/1998 | Dombrowski et al. | 606/61 |
| 5,720,751 A | * | 2/1998 | Jackson | 606/86 |
| 5,910,141 A | * | 6/1999 | Morrison et al. | 606/61 |
| 6,036,692 A | * | 3/2000 | Burel et al. | 606/61 |

* cited by examiner

*Primary Examiner*—Henry Bennett
*Assistant Examiner*—Nihir Patel
(74) *Attorney, Agent, or Firm*—Greenblum & Bernstein, P.L.C.

(57) ABSTRACT

A slider 37 having a rod-pressing portion 35 for pressing a rod 23 into a rod-engaging recess 25 is movably provided on a holder body 27 having the rod-engaging recess 25. The holder body 27 includes a pressing state holding mechanism for relatively moving the slider 37 with respect to the holder body 27 to hold the rod 23 in a state in which the rod 23 is pressed against the rod-engaging recess 25 by the rod-pressing portion 35. The pressing state holding mechanism includes a screw rod movably, detachably and threadedly engaged with a screw hole formed in the holder body 27. A tip end of the screw rod 45 and the slider 37 connected to each other such that they permit rotation of the screw rod 45 with respect to the slider 37 but move integrally with respect to the holder body 27, and the slider 37 can be attached to and detached from the slider 37.

5 Claims, 4 Drawing Sheets

ROD GRIPPER

BACKGROUND OF THE INVENTION

The present invention relates to a rod gripper for holding a coapting rod which coapts bones such as thoracic vertebrae and lumbar vertebrae, and more particularly, to a rod gripper capable of easily holding the rod even if its diameter is slightly varied.

When a pair of implants are threadedly embedded into separated centrums such as thoracic vertebras and lumbar vertebrae, and opposite ends of a coapting rod are to be supported and fixed by the pair of implants, a rod gripper is generally used for grasping, positioning and setting the rod such that the opposite ends of the rod are engaged with and supported by the pair of implants.

In a conventional gripper investigated by the present inventors and shown in FIG. 1, intermediate portions of a pair of hafts 1A and 1B are pivoted by a pin 3 so that tip ends of the hafts 1A and 1B can open and close, and engaging recesses 7 for grasping a rod 5 are formed in the tip ends in an opposed manner. A lock piece 11 is pivotally connected to a base of the one haft 1A through a hinge pin 9. This lock piece 11 is formed with lock recesses 13 at appropriate distances from one another, and the lock recesses 13 can lock a base end of the other haft 1B. The lock piece 11 is biased by a leaf spring 15 mounted to the one haft 1A so that the engaging state between the base end of the other haft 1B and the lock recesses 13 is maintained.

In the conventional rod gripper of the above structure, if the lock piece 11 is turned in a direction of an arrow A to release the engagement between the lock recesses 13 and the base end of the haft 1B, the tip ends of the pair of hafts 1A and 1B can open and close, and the rod 5 can be sandwiched between the engaging recesses 7 formed on the tip ends. After the rod 5 is sandwiched between the engaging recesses 7, if the lock piece 11 is turned in a direction opposite from the arrow A to lock the base end of the haft 1B into one of the lock recesses 13, the pair of hafts 1A and 1B are locked to hold the rod 5.

In the conventional rod gripper, since the lock recesses 13 are stepwisely formed on the lock piece 11, if the base end of the haft 1B is locked into the lock recess 13 of the lock piece 11, the engaging recesses 7 on the tip ends can not sandwich the rod 5 strongly. That is, if a diameter of the rod 5 is slightly varied, the rod can not be held reliably.

Further, the conventional rod gripper has the following problem. That is, in order to obtain a great grasping force, it is necessary that a distance between the pin 3 and the base ends of the hafts 1A and 1B is longer than a distance between the pin 3 and the tip ends of the hafts 1A and 1B. Further, in the conventional rod gripper, the hafts 1A and 1B pivotally turn around the pin 3, thereby grasping the rod. Therefore, it is necessary to secure a width between the hafts 1A and 1B and it is difficult to make the entire structure thin, long and compact. Further, the pair of the hafts 1A and 1B, the lock piece 11, the leaf spring 15 and the like can not be disassembled, and it is troublesome to clean every nock and corner.

SUMMARY OF THE INVENTION

The present invention has been accomplished in view of the above problems, and according to a first aspect of the present invention, there is provided a rod gripper comprising a holder body provided at its tip end with a rod-engaging recess, a slider provided at its tip end with a rod-pressing portion for pressing a rod in an opposed manner to the rod-engaging recess, and a pressing state holding mechanism fore moving the slider relative to the holder body to hold the rod in a state in which the rod is pressed against the rod-engaging recess by the rod-pressing portion.

With the first aspect, by relatively moving the slider with respect to the holder body, the rod is pressed toward the rod-engaging recess by the rod-pressing portion. Therefore, grasping forces (pressing forces) are centered in one direction without being dispersed, and it is possible to strongly grasp the rod and maintain the grasping state.

According to a second aspect of the present invention, in the rod gripper of the first aspect, the pressing state holding mechanism comprises a screw hold formed in the holder body, and a screw rod movably, detachably and threadedly engaged with the screw hole such that the screw rod can be detached, and wherein the screw rod is rotatably connected to the slider and can move integrally with the slider with respect to the holder body.

With the second aspect, as the screw rod is threadedly moved with respect to the screw hole, the rod-pressing portion formed on the tip end of the slider continuously moves in a direction of the rod-engaging recess (direction of the threadedly rotating direction) integrally with and in parallel to the screw rod. In reply to this movement, a distance between the rod-engaging recess and the rod-pressing portion is also continuously varied and thus, the distance can be adjusted in a stepless manner, and even if the diameter of the rod is slightly varied, such variation can be handled easily.

According to a third aspect of the present invention, in the rod gripper of the first aspect, the slider is attachable and detachable with respect to the holder body.

With the third aspect, since the slider is detachable from the holder body, the rod gripper can easily be disassembled and cleaned sufficiently.

According to a fourth aspect of the present invention, in the rod gripper of the first aspect, the slider includes a support piece engaged with and supported by a guide slit provided in the holder body such that the support piece can move along the guide slit.

With the fourth aspect, the slider can precisely move along a path orientated by the guide slit in a state in which the slider is engaged with and supported by the support piece. Therefore, the effect of the first and the second aspects can be ensured more reliably.

According to a fifth aspect of the present invention, in the rod gripper of the second aspect, the slider includes an engaging hole which is rotatably engaged with a locking portion provided on a tip end of the screw rod.

With the fifth aspect, the locking portion formed on the tip end of the screw rod and the engaging hole provided in the slider are rotatably engaged with each other. Therefore, the screw rod can rotate with respect to the slider, and the effect of the second aspect can be ensured more reliably.

As will be understood from the above description, according to the present invention, even if a diameter of the rod is slightly varied, the variation can be handled easily, and the rod can be strongly grasped, and the grasping state can be maintained easily. Further, the rod gripper can be disassembled and cleaned easily, and the above-described problems of the prior art can be overcome.

DESCRIPTION OF THE PREFERRED EMBODIMENT

Figure 1:
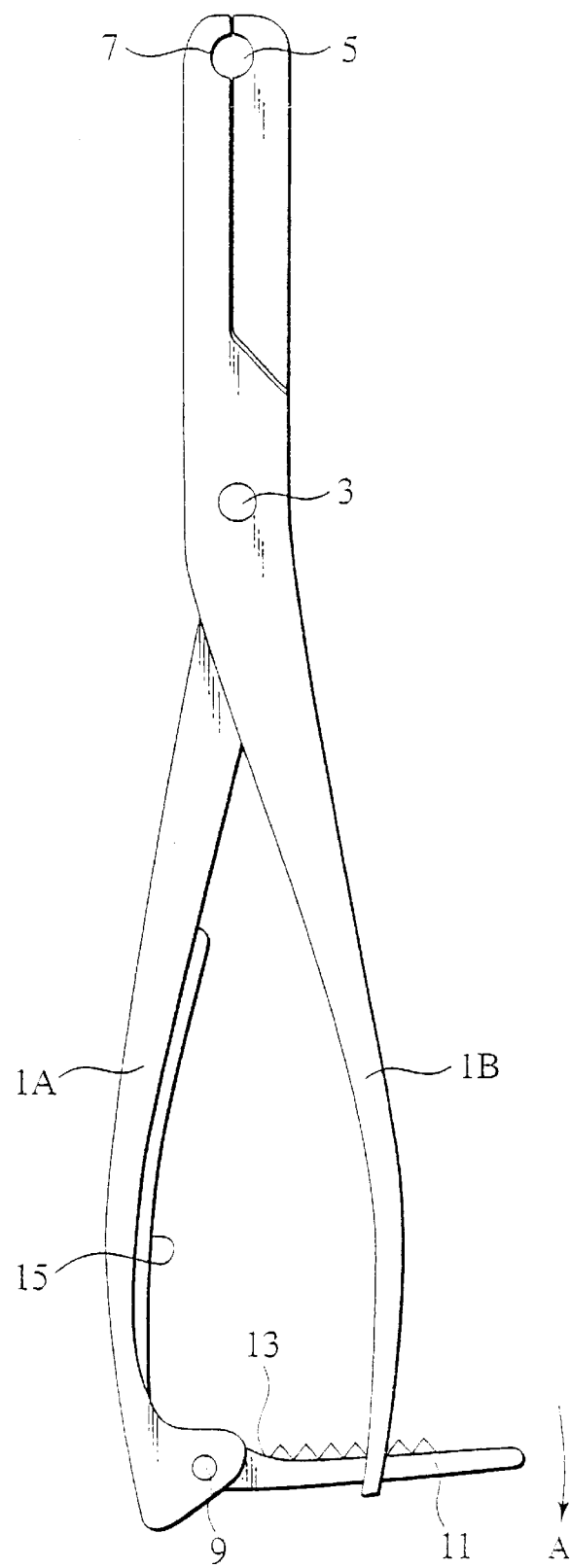
FIG. 1 is an explanatory view of a conventional rod gripper.
Figure 2:
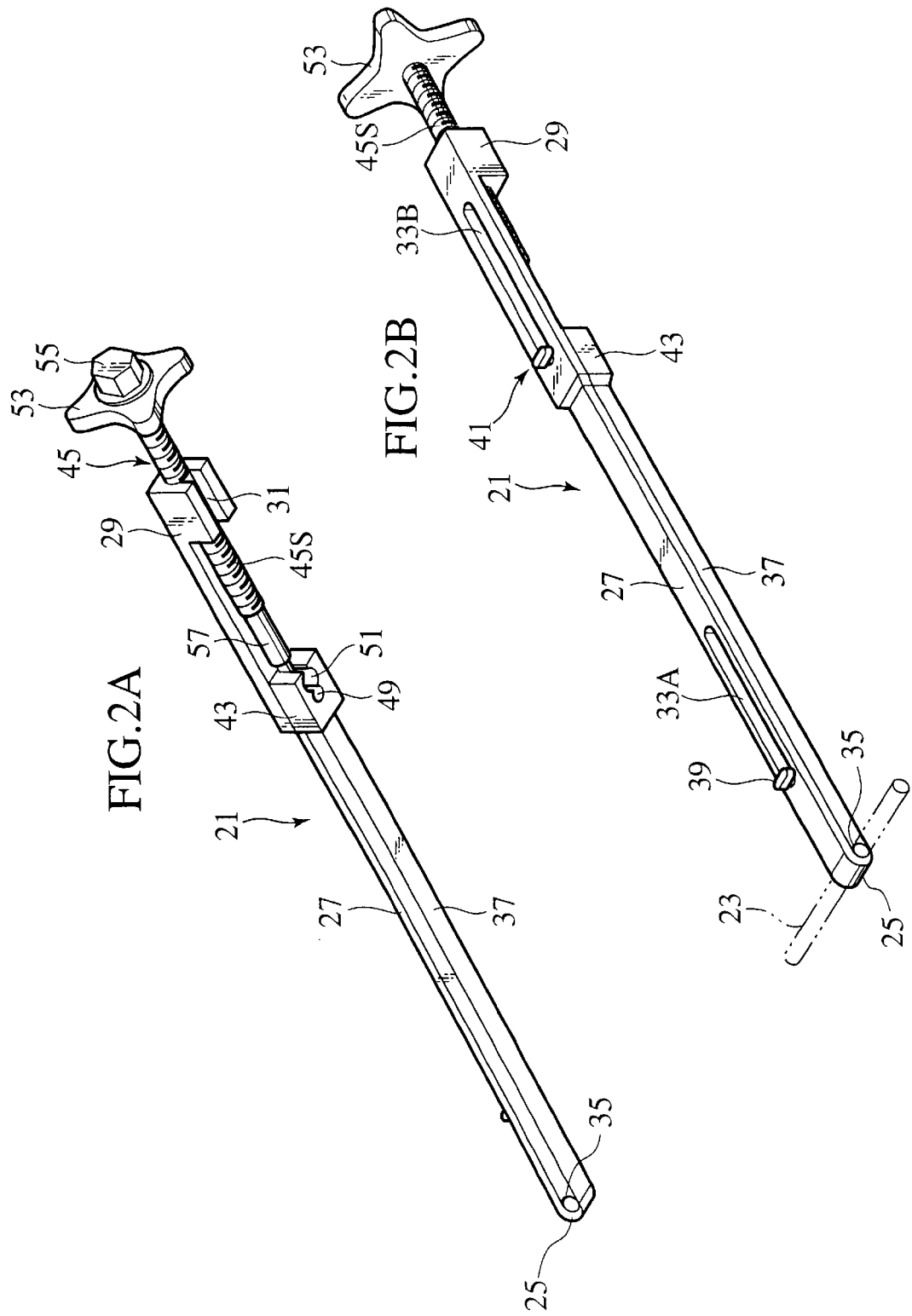
FIGS. 2A and 2B are explanatory perspective views of a rod gripper according to an embodiment of the present invention.

Referring to FIGS. 2A and 2B, a rod gripper 21 of the present embodiment, when a pair of implants (not shown) are threadedly embedded into separated centrums such as thoracic vertebras and lumbar vertebrae, and a rod 23 whose opposite end portions are supported by the pair of implants are to be set to the implant, a rod gripper 21 grasps the rod 23.

The rod gripper 21 includes a thin and long holder body 27 provided at its tip end with a semi-circular rod-engaging recess 25 for engaging and holding the rod 23. A base end of the holder body 27 is formed with a nut 29 having a female screw as a thread hole. The nut 29 is formed with a slit 31 in a longitudinal direction of the holder body 27. Longitudinal guide slits 33A and 33B are formed several portions of intermediate portions of the holder body 27 in its longitudinal direction.

The holder body 27 is provided with a thin and long slider 37 such as to be opposed to the rod-engaging recess 25 formed on the holder body 27. The slider 37 is formed at its tip end with a semi-circular recess as a rod-pressing portion 35. The slider 37 can move in a longitudinal direction of the holder body 27. That is, the slider 37 is movably supported by the holder body 27 through support pieces 39 and 41 which are movably engaged with and supported by the guide slits 33A and 33B.

Figure 3:
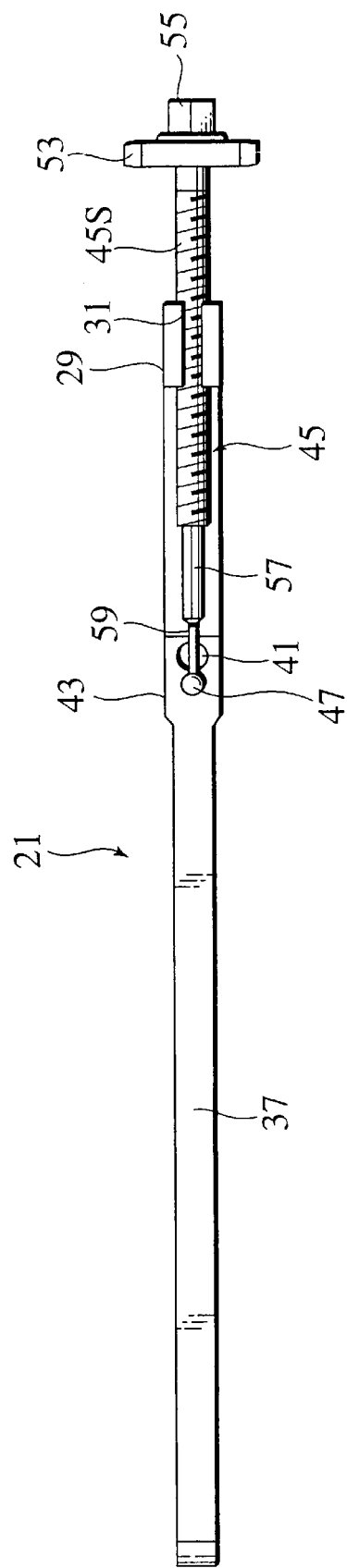
FIG. 3 is an explanatory bottom view of the rod gripper of the embodiment of invention.
Figure 4:
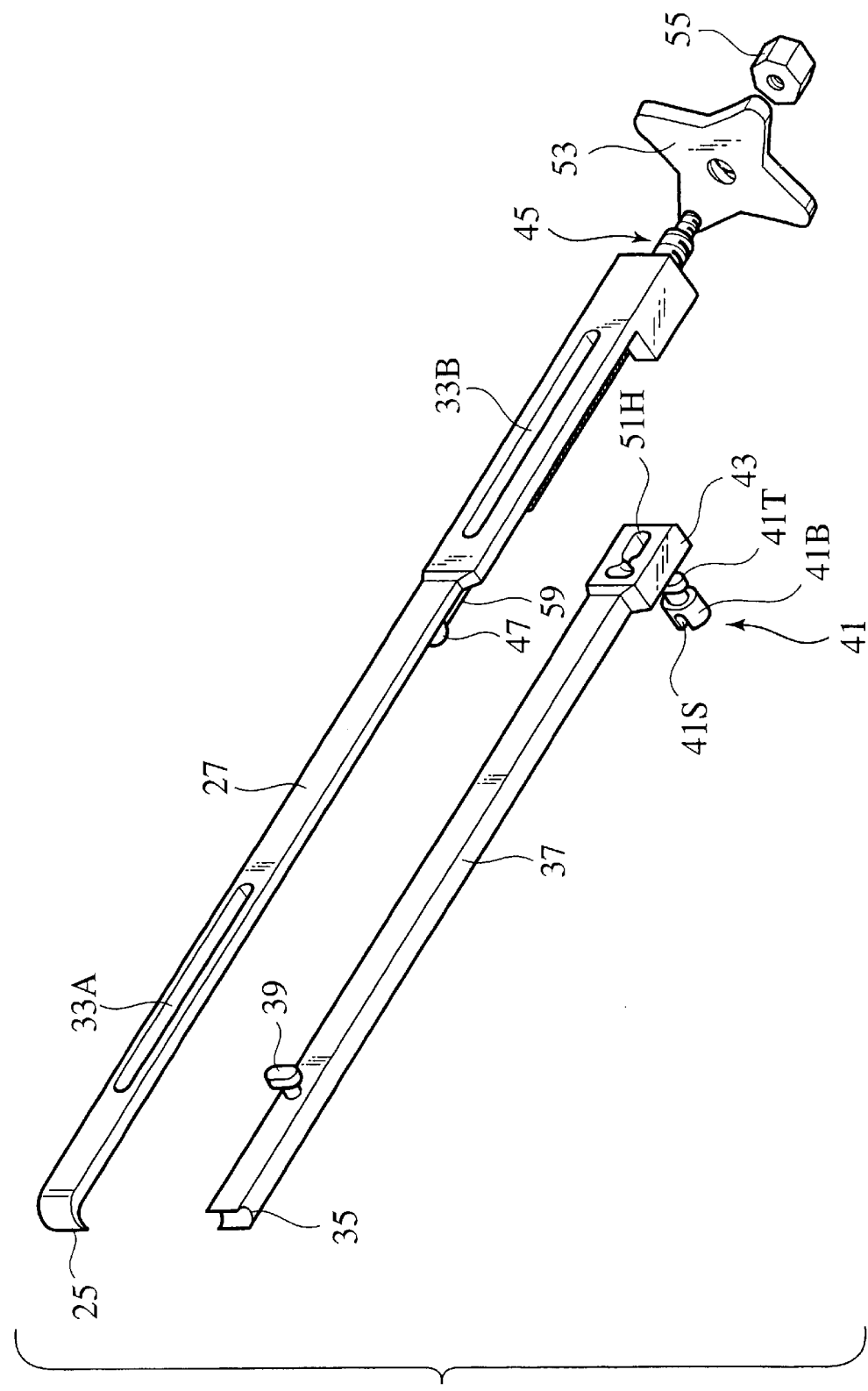
FIG. 4 is an explanatory exploded view of the rod gripper of the embodiment of invention.

More specifically, as shown in FIG. 4, the T-shaped support piece 39 is integrally fixed to a tip end of the slider 37, and the slider 37 is formed at its base end with an enlarged portion 43. The enlarged portion 43 is formed with an engaging hole 49 into which a locking portion 47 (see FIG. 3) is engaged. The locking portion 47 is formed on a tip end of a screw rod 45 (see FIGS. 2A and 2B) for moving the slider 37. The enlarged portion 43 is formed at its portion closer to its end face than the engaging hole 49 with a support piece-engaging hole 51 into which the support piece 41 is engaged. The engaging hole 49 and the support piece engaging hole 51 are connected to each other with a slight slit, and the support piece engaging hole 51 is in communication with and opened into an end face of the enlarged portion 43 through a slight slit.

The screw rod 45 includes a screw 45S which can be threadedly engaged with the nut 29. An operation knob 53 is detachably mounted to a base end of the screw 45S through a fastening tool 5 such as a nut. A shaft 57 is formed on a tip end of the screw 45S. The shaft 57 is slightly smaller in diameter than a width of the slit 31 of the nut 29 and slightly longer than a longitudinal size of the nut 29. The locking portion 47 is formed on a tip end of a small-diameter portion 59 which is formed on a tip end of the shaft 57 in a thin and long manner. The locking portion 47 is formed into a spherical shape which is larger than the small-diameter portion 59 in diameter.

As shown in FIG. 4, the support piece 41 includes a columnar body portion 41B which can engage into the support piece engaging hole 51. The support piece 41 includes a T-shaped top portion 41T which can engage the guide slit 33B. The body portion 41B is formed with a slit 41S in a direction perpendicular to a T-shaped portion of the top portion 41T.

In the above-described structure, when these constituent members are in their disassembled states, if the T-shaped support piece 39 provided on the slider 37 is inserted through the guide slit 33A formed in the holder body 27, and the holder body 27 and the slider 37 are superposed on each other such that their longitudinal directions coincide with each other, the rod-engaging recess 25 formed on the tip end of the holder body 27 and the rod-pressing portion 35 formed on the tip end of the slider 37 are assembled to each other such that they are opposed to each other.

Next, the support piece 41 is engaged with the support piece engaging hole 51 formed in the enlarged portion 43 of the slider 37, the T-shaped top portion 41T is projected from a long hole 51H which is in communication with the support piece engaging hole 51, and the top portion 41T is inserted into the guide slit 33B. Then, the enlarged portion 43 of the slider 37 is held in a state in which the enlarged portion 43 is adjacent to the nut 29 of the base end of the holder body 27. The locking portion 47 of the tip end of the screw rod 45 is engaged with the engaging hole 49 of the enlarged portion 43, a small-diameter portion 59 of the screw rod 45 is engaged with the slit 41S of the support piece 41, the shaft 57 of the screw rod 45 passes through the slit 31 of the nut 29 so that the shaft 57 is set in the female screw.

Thereafter, if the operation knob 53 mounted to the screw rod 45 is rotated, and the screw 45S of the screw rod 45 is threadedly engaged with the female screw of the nut 29, each of the constituent members is assembled as shown in FIGS. 2A and 2B. In this assembled state, the slider 37 and the screw rod 45 permit rotation of the screw rod 45 with respect to the slider 37, but the holder body 27 moves integrally in its longitudinal direction. As already understood, since the rod gripper can be assembled as described above, the rod gripper 21 of the present embodiment can be disassembled into each of the constituent members, and it is possible to easily clean the four corners of the rod gripper.

As described above, in a state in which the constituent members are assembled, if the operation knob 53 is rotated, the slider 37 can be moved back and forth in its longitudinal direction with respect to the holder body 27, and the rod 23 can be grasped strongly between the rod-engaging recess 25 formed on the tip end of the holder body 27 and the rod-pressing portion 35 formed on the tip end of the slider 37.

At that time, the slider 37 is moved with respect to the holder body 27 by a screw mechanism in which the screw rod 45 is threadedly engaged with the nut 29 of the holder body 27. Therefore, a distance between the rod-engaging recess 25 and the rod-pressing portion 35 can be adjusted in a stepless manner, and even if a diameter of the rod 23 is slightly varied due to manufacturing error of the rod 23, it is easy to deal with the variation, and it is possible to strongly fasten and grasp.

Further, since the slider 37 is moved by the screw mechanism described above, it is easy to hold the rod 23 in a state in which the rod 23 presses the rod-engaging recess 25 and thus, the screw mechanism can be called a pressing state holding mechanism.

As already understood, since both the holder body 27 and the slider 37 are thin and long. Therefore, in a state in which an operator holds the rod 23 during medical practice, an area occupied by the rod is small with respect to other medical equipment in the vicinity of the operator's hand or around a patient and as a result, it is possible to restrain the holder body 27 and the slider 37 from interfering with other members.

What is claimed is:

1. A rod gripper, comprising:

a holder body provided at its tip end with a rod-hooking portion having a first recess hooking a rod, a slider provided at its tip end with a rod-pressing portion having a second recess facing said first recess of said rod-hooking portion, a guiding mechanism guiding said slider in a position where said second recess of said rod-pressing portion is joined to said first recess of said rod-hooking portion via said rod, and a pressing state holding mechanism holding said rod in a state in which said rod is pressed between said first recess of said rod-hooking portion and said second recess of said rod-pressing portion at said position, wherein said guiding mechanism comprises a guide slit provided in said holder body, and a support piece provided with said slider and, engaged with and supported by said guide slit such that said support piece can move along said guide slit.

2. The rod gripper according to claim 1, wherein said pressing state holding mechanism comprises a screw hole formed in said holder body, and a screw rod movably, detachably and threadedly engaged with said screw hole such that said screw rod can be detached, and wherein said screw rod is rotatably connected to said slider and can move integrally with said slider with respect to said holder body.

3. The rod gripper according to claim 1, wherein said slider is attachable and detachable with respect to said holder body.

4. A rod gripper, comprising:

a holder body provided at its tip end with a rod-engaging recess, a slider provided at its tip end with a rod-pressing portion for pressing a rod in an opposed manner to said rod-engaging recess, a pressing state holding mechanism for moving said slider relative to said holder body to hold said rod in a state in which said rod is pressed against said rod-engaging recess by said rod-pressing portion, and wherein said pressing state holding mechanism comprises:

a screw hole formed in said holder body, and a screw rod movably, detachably and threadedly engaged with said screw hole such that said screw rod can be detached, and wherein said screw rod is rotatably connected to said slider and can move integrally with said slider with respect to said holder body, and wherein said slider includes an enlarged portion having an engaging hole at its base end, which is rotatably engaged with a spherical shaped locking portion provided on a tip end of said screw rod.

5. The rod gripper according to claim 4, wherein said slider is attachable and detachable with respect to said holder body.

* * * * *

UNITED STATES PATENT AND TRADEMARK OFFICE
CERTIFICATE OF CORRECTION

PATENT NO. : 6,790,208 B2
DATED : September 14, 2004
INVENTOR(S) : K. Oribe et al.

It is certified that error appears in the above-identified patent and that said Letters Patent is hereby corrected as shown below:

Title page,
Item [56], References Cited, U.S. PATENT DOCUMENTS, the following should be included:
-- 1,454,319    05/08/23    Hamer --
FOREIGN PATENT DOCUMENTS, the following should be included:
-- 2657246    07/26/91    France --

Column 5,
Line 24, "slider and," should be -- slider, and --.

Signed and Sealed this

Twenty-fourth Day of May, 2005

JON W. DUDAS
*Director of the United States Patent and Trademark Office*